Figure 3:
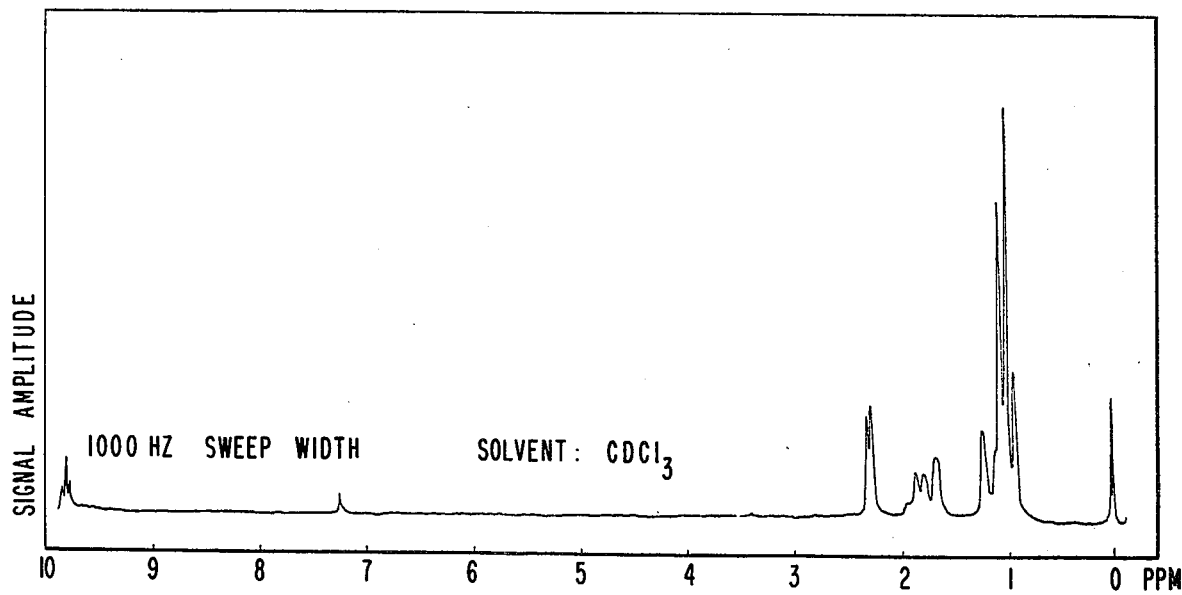

United States Patent [19]

Mookherjee et al.

[11] 4,014,823
[45] Mar. 29, 1977

[54] π-TRICYCLENE-9-ALKANONE PERFUMES

[75] Inventors: Braja Dulal Mookherjee, Holmdel; Venkatesh Kamath, Red Bank, both of N.J.; Edward J. Shuster, Brooklyn, N.Y.

[73] Assignee: International Flavors & Fragrances Inc., New York, N.Y.

[22] Filed: Jan. 5, 1976

[21] Appl. No.: 646,608

Related U.S. Application Data

[63] Continuation-in-part of Ser. No. 556,862, March 10, 1975, Pat. No. 3,944,621.

[52] U.S. Cl. .............................. 252/522; 260/586 G
[51] Int. Cl.$^2$ ............................................ L11B 9/00
[58] Field of Search ................. 252/522; 260/586 G

[56] References Cited

UNITED STATES PATENTS

| | | |
|---|---|---|
| 2,730,548 | 1/1956 | Bruestone et al. ............ 260/586 G |
| 3,478,114 | 11/1969 | Lewis et al. ........................ 252/522 |
| 3,626,015 | 12/1971 | Lewis et al. .................... 260/586 G |
| 3,662,008 | 5/1972 | Kretschmar et al. .............. 252/522 |
| 3,673,261 | 6/1972 | Kretschmar et al. .............. 252/522 |
| 3,673,263 | 6/1972 | Fanta et al. ........................ 252/522 |
| 3,860,635 | 1/1975 | Kitchens ........................ 260/586 G |

*Primary Examiner*—Veronica O'Keefe
*Attorney, Agent, or Firm*—Arthur L. Liberman; Harold Haidt; Franklin D. Wolffe

[57] ABSTRACT

Processes and compositions are described for altering the aroma of consumable products including perfumes, perfume compositions and perfumed articles utilizing as the essential ingredient a novel organic π-tricyclene derivative having one of the formulae:

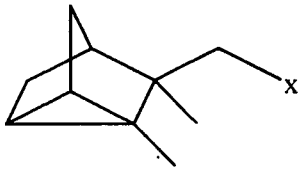

wherein X is a moiety selected from the group consisting of:

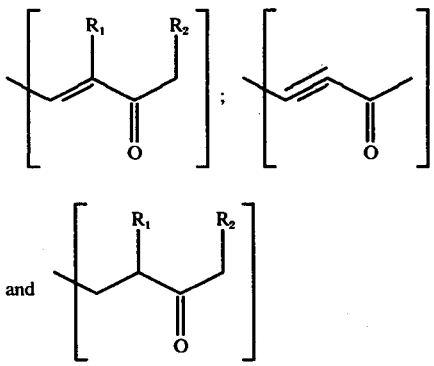

and wherein $R_1$ and $R_2$ are each selected from the group consisting of hydrogen and methyl, at least one of $R_1$ or $R_2$ being hydrogen.

4 Claims, 11 Drawing Figures

FIG. I
EXAMPLE I
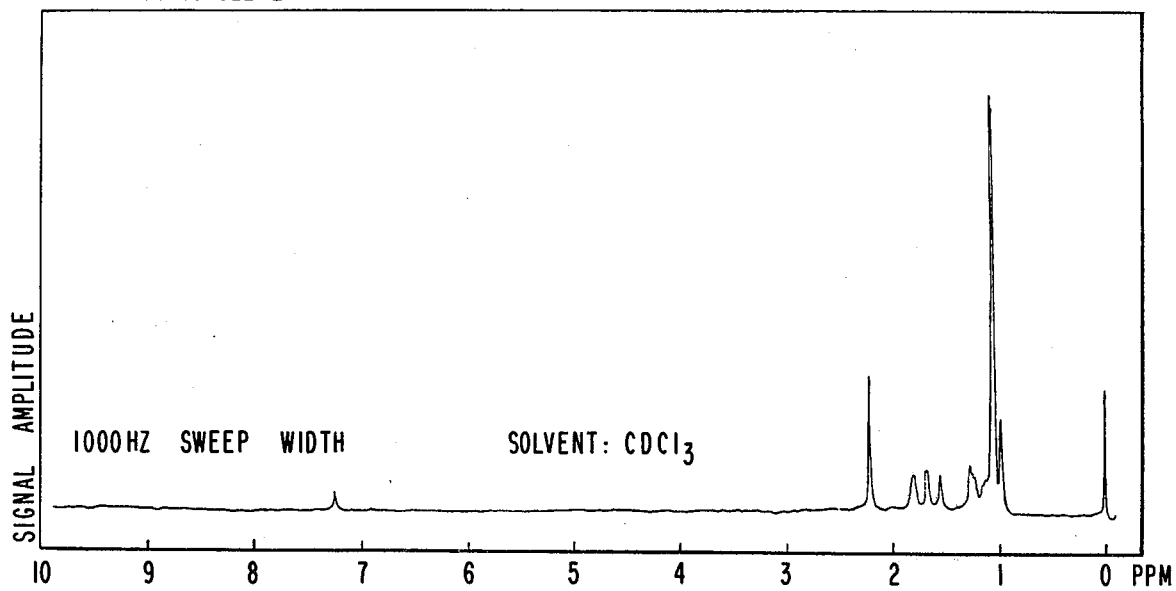
FIG. 2
EXAMPLE I
π-CYANOTRICYCLENE
IR SPECTRUM
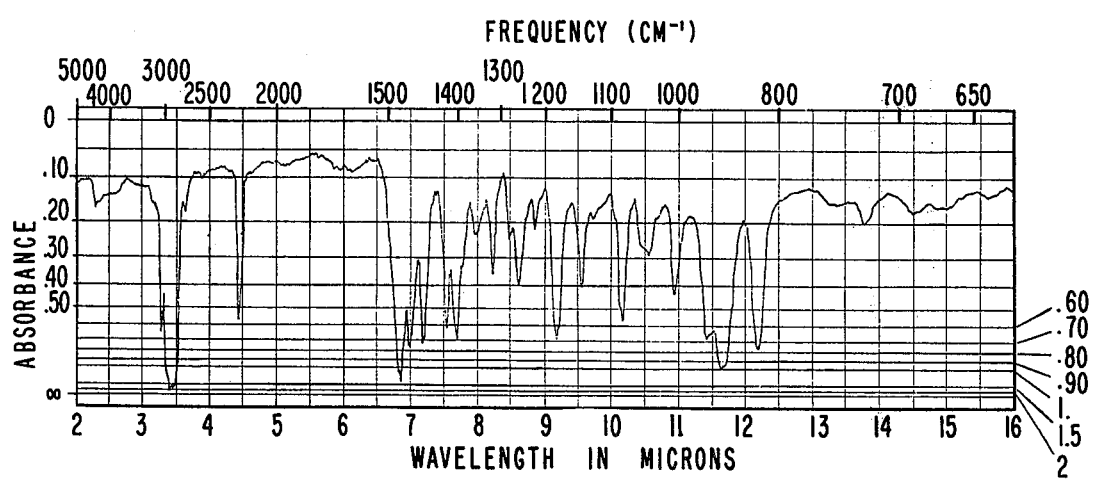

EXAMPLE II

EXAMPLE II
NORTRICYCLOEKASANTALAL
IR SPECTRUM

NMR SPECTRUM
EXAMPLES III AND VIII, FRACTION 63, PEAK 3a
1,7-DIMETHYL-7(1-PENT-2-EN-4-ONYL) NORTRICYCLENE

EXAMPLES III AND VIII, FRACTION 63, PEAK 3a
1,7-DIMETHYL-7(1-PENT-2-EN-4-ONYL) NORTRICYCLENE

FIG.7
EXAMPLE V
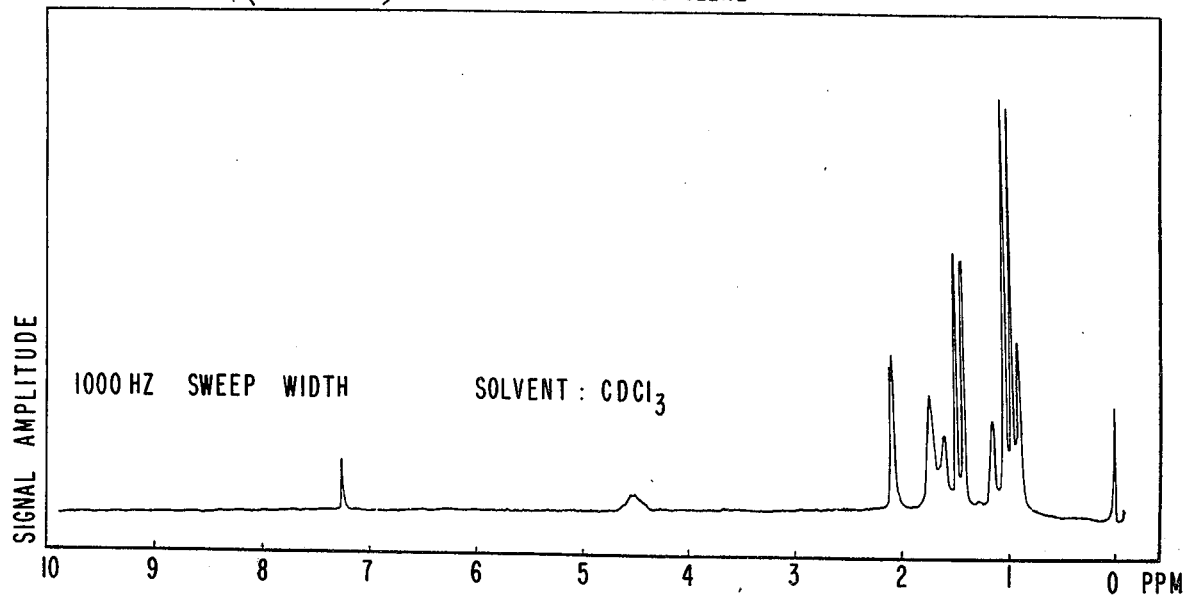
NMR SPECTRUM
1,7-DIMETHYL-7(1-[4'-HYDROXY] PENT-2-YNYL) NORTRICYCLENE
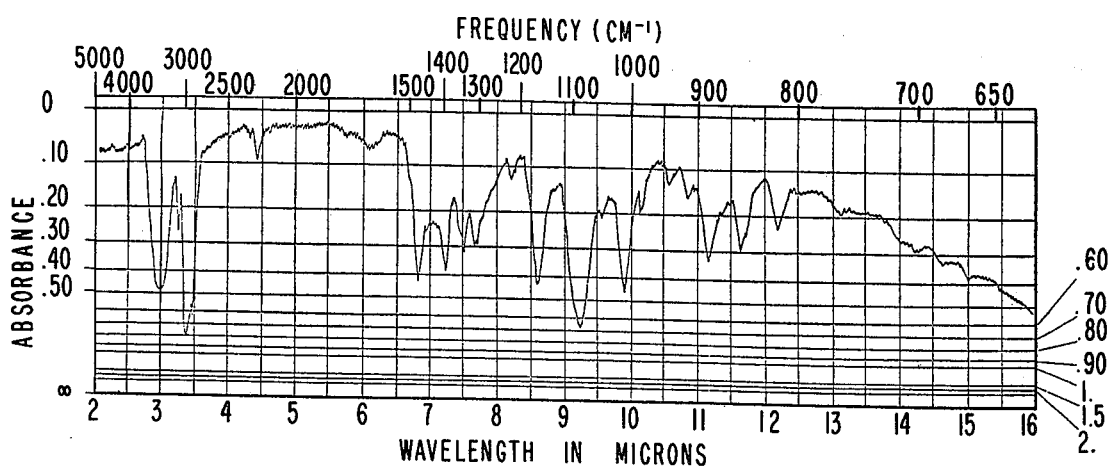
FIG.8
EXAMPLE V
IR SPECTRUM
1,7-DIMETHYL-7(1-[4'-HYDROXY] PENT-2-YNYL) NORTRICYCLENE

FIG. 9
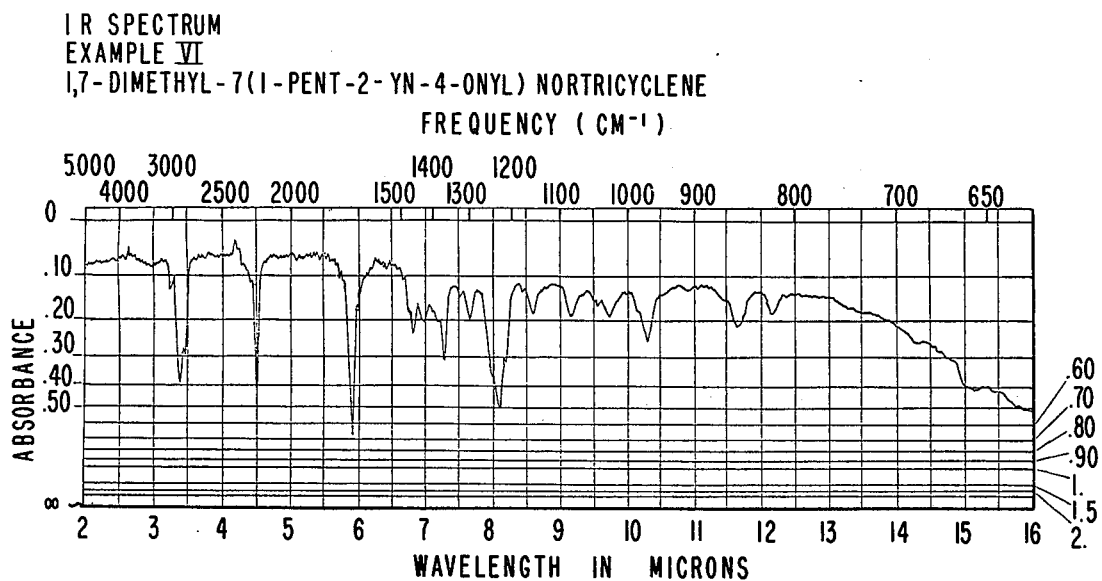
IR SPECTRUM
EXAMPLE VI
1,7-DIMETHYL-7(1-PENT-2-YN-4-ONYL) NORTRICYCLENE
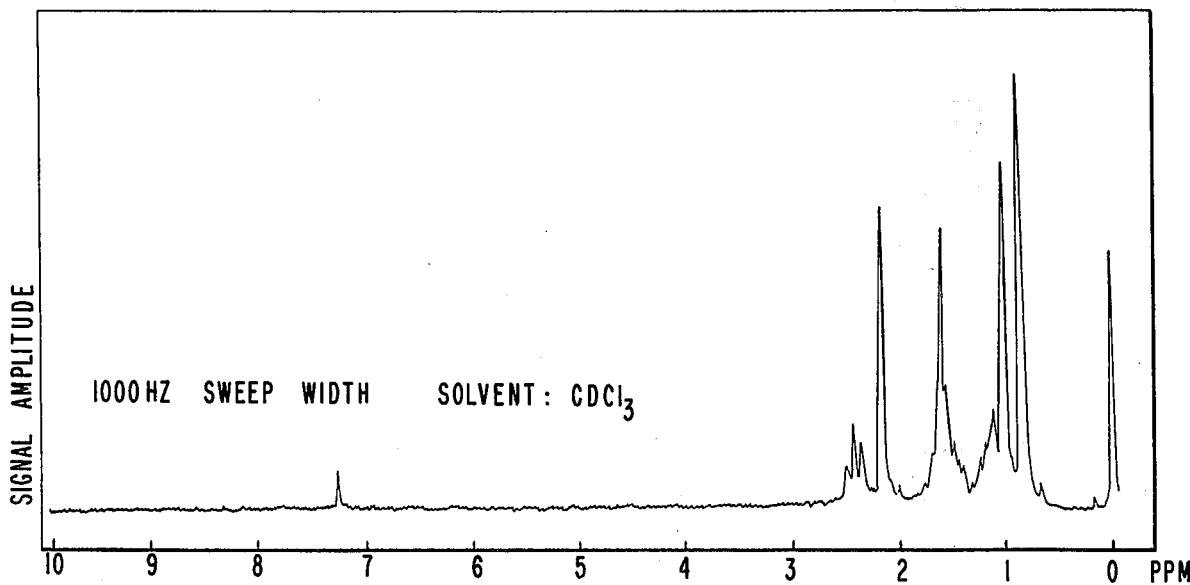
NMR SPECTRUM
EXAMPLES VII AND VIII, FRACTION 41, PEAK 7C
1,7-DIMETHYL-7(1-PENTAN-4-ONYL) NORTRICYCLENE
FIG. 10

EXAMPLE VII AND EXAMPLE VIII
FRACTION 41, PEAK 7C
1,7-DIMETHYL-7(1-PENTAN-4-ONYL) NORTRICYCLENE

IR SPECTRUM

π-TRICYCLENE-9-ALKANONE PERFUMES

This Application is a continuation-in-part of application for U.S. Letters Patent No. 556,862, filed on Mar. 10, 1975, now U.S. Pat. No. 3,944,621 issued on Mar. 16, 1976.

BACKGROUND OF THE INVENTION

East Indian sandalwood oil has heretofore been available only from 60–80 year old East Indian sandalwood trees. This oil and various individual components of the oil are highly valued perfume bases and are used in large quantities by the perfume industry. The oil, however, is expensive and is in limited, and sometimes sporadic, supply. For this reason, a continuous effort has been made to synthesize the various components of sandalwood oil or similar synthetic materials which possess the several desirable nuances (e.g., woody, oily, green) of sandalwood oil.

The processes presented herein for preparing various sandalwood aroma components represent a portion of an extensive effort to obtain various components of sandalwood oil as well as substitutes therefor. Other processes and components related to the synthesis of sandalwood oil aroma-like components are described in the following publications:

i. U.S. Pat. No. 3,478,114 issued on Nov. 11, 1969
  Title: PROCESS FOR MAKING ALPHA-SANTALOL
  Covers the process:

ii. U.S. Pat. No. 3,662,007 issued on May 9, 1972
  Title: PROCESS FOR PREPARING DIHYDRO-BETA-SANTALOL FROM 3-ENDO-METHYL-3-EXO (4'-METHYL-5'-HYDROXYPHENYL) NORCAMPHOR Covers the process for preparing dihydrobeta-santalol from 3-endo-methyl-3-exo (4'-methyl-5'-hydroxypentyl) norcamphor comprising the steps (1) reacting 1-endo methyl-3-exo(4'-methyl-5'-hydroxypentyl) norcamphor with either boric acid or boric anhydride to obtain the borate ester of 3-endo-methyl-3-exo(4'-methyl-5'-hydroxypentyl) norcamphor, and (2) reacting the borate ester reaction product of Step (1) with a phosphorous compound such as methyltriphenylphosphonium bromide and subsequently hydrolyzing the reaction product with water to obtain dihydro-beta-santalol.

iii. U.S. Pat. No. 3,662,008 issued by May, 9, 1972
  Title: PROCESS FOR PREPARING BETA-SANTALOL FROM 3-METHYLNORCAMPHOR Covers the process for preparing beta-santalol from 3-methylnorcamphor comprising the steps of (1) alkylating 3-methylnorcamphor in strong base with an allyl halide; (2) reacting the reaction product of Step (1) with a methylmetallic compound, such as methyllithium, followed by hydrolysis; (3) brominating the reaction product of Step (2); (4) dehydrobrominating the reaction product of Step (3) with a base, such as sodium amide; (5) dehydrating the reaction product of Step (4) with a dehydrating agent, such as thionyl chloride; (6) reacting the reaction product of Step (5) with a compound, such as di(sec.-iso-amyl)borane followed by an oxidation; (7) reacting the reaction product of Step (6) with (carbethoxyethylidene) triphenylphosphorane; and (8) reducing the reaction product of Step (7) with a reducing agent such as lithium aluminum hydride, to obtain beta-santalol.

iv. U.S. Pat. No. 3,673,261 issued on June 27, 1972
  Title: PERFUME COMPOUNDS AND PROCESS FOR PREPARING SAME Covers the use in perfumery compounds having the following structures:

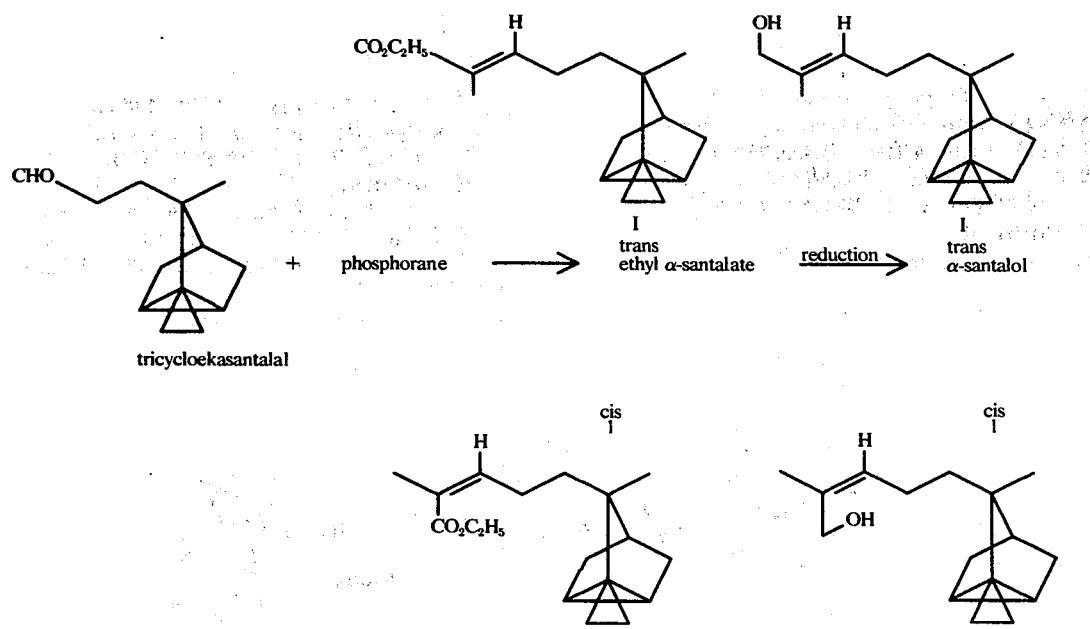

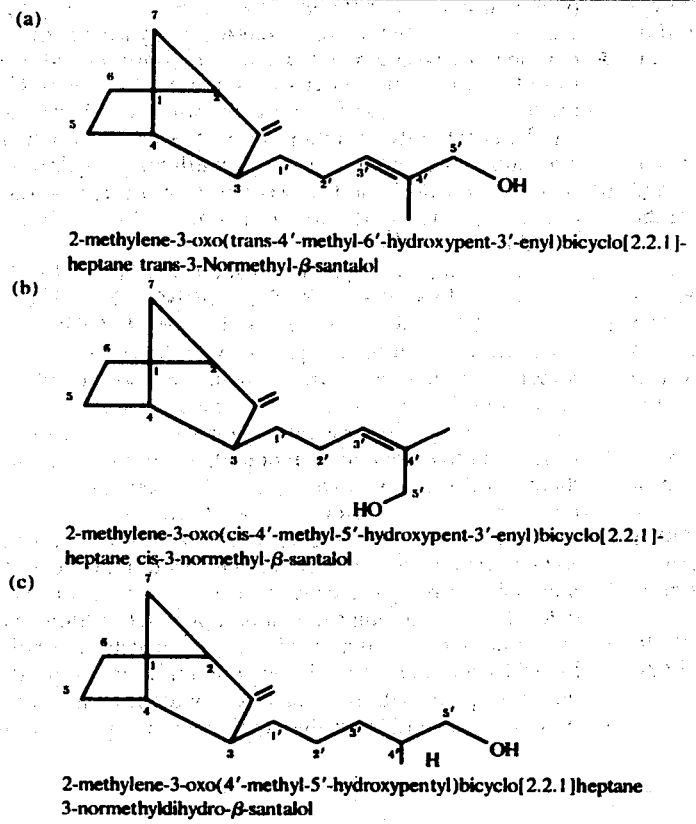

(a) 2-methylene-3-oxo(trans-4'-methyl-6'-hydroxypent-3'-enyl)bicyclo[2.2.1]-heptane trans-3-Normethyl-β-santalol (b) 2-methylene-3-oxo(cis-4'-methyl-5'-hydroxypent-3'-enyl)bicyclo[2.2.1]-heptane cis-3-normethyl-β-santalol (c) 2-methylene-3-oxo(4'-methyl-5'-hydroxypentyl)bicyclo[2.2.1]heptane 3-normethyldihydro-β-santalol v. U.S. Pat. No. 3,673,263 issued on June 27, 1972
Title: DIHYDRO-BETA-SANTALOL AND PROCESS FOR PREPARING DIHYDRO-BETA-SANTALOL FROM 3-ENDO-METHYL-3-EXO(4'-METHYL-5'-HYDROXYPENTYL) NORCAMPHOR vi. U.S. Pat. No. 3,673,266 issued on June, 27, 1972
Title: PROCESS FOR PREPARING DIHYDRO-BETA-SANTALOL FROM 3-ENDO-METHYL-3-EXO (4'-METHYL-5'-HYDROXYPENTYL) NORCAMPHOR vii. Corey, et al., J.Am.Chem.Soc. 79, 5773 (1957)
Title: THE SYNTHESIS OF ALPHA-SANTALENE AND OF TRANS-Δ 11,12 -ISO-ALPHA-SANTALENE Describes the following process sequence:

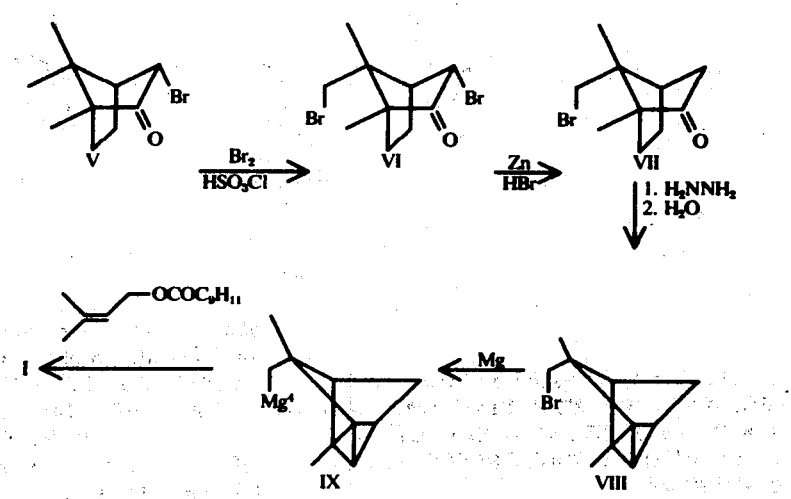

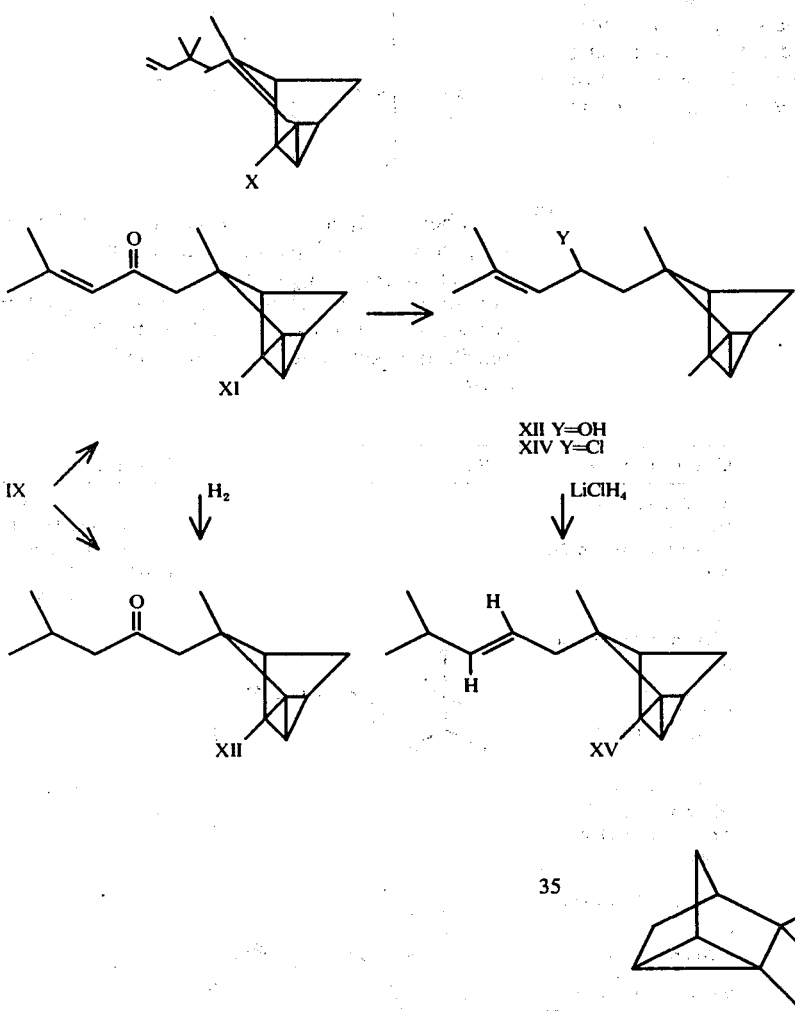

However, none of the above processes explicitly or implicitly represent what are today deemed to be economically feasible techniques for providing the important and novel sandalwood aroma components having the generic structure:

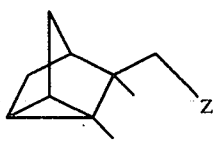

wherein Z is a moiety selected from the group consisting of:

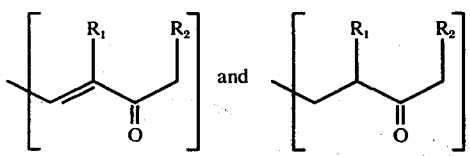

Furthermore, the structures of sandalwood aroma components set forth in the above-mentioned prior art are chemically different in kind from the novel compounds of this invention which have the generic structure:

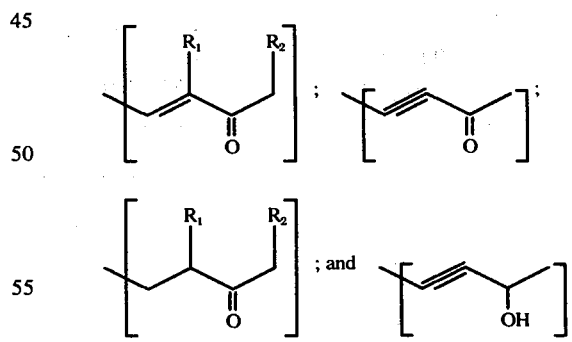

wherein X is a moiety selected from the group consisting of:

and wherein $R_1$ and $R_2$ are each selected from the group consisting of hydrogen and methyl, at least one of $R_1$ and $R_2$ being hydrogen. The novel compounds of this invention have properties considered to be unobvious and advantageous over the compounds set forth in the aforecited prior art.

THE INVENTION

It has now been determined that several π-tricyclene derivatives are capable of imparting notes important to sandalwood fragrance to various consumable materials. Briefly, our invention contemplates altering the fragrance of such consumable materials as perfumes, perfume formulations and perfumed articles by adding thereto a small but effective amount of at least one of the novel π-tricyclene derivatives having a generic structure:

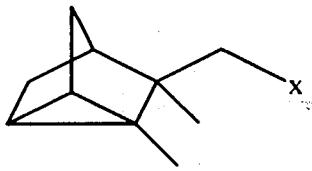

wherein X is a moiety selected from the group consisting of:

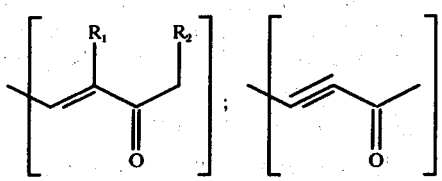

and

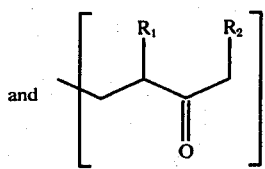

and wherein $R_1$ and $R_2$ are each selected from the group consisting of hydrogen and methyl, at least one of $R_1$ or $R_2$ being hydrogen.

Examples of π-tricyclene derivatives useful in the practice of our invention and particularly useful in contributing key notes to sandalwood aromas are as follows:

| Compound Name | Structure | Olfactory Properties |
| --- | --- | --- |
| 5-(2,3-dimethyl-tricyclo(2.2.1.0$^{2,6}$) hept-3-yl)3-penten-2-one or tricyclene-9-butenone or 1,7-dimethyl-7-(1-pent-2-en-4-onyl) nortricyclene | 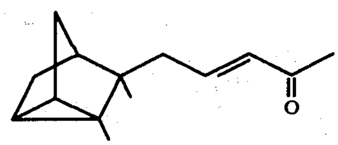 | Sweet, woody, oily, sweaty, sandalwood aroma with "sexy-woody", amber green and orrisy nuances. |
| 5-(2,3-dimethyl tricyclo(2.2.1.0$^{2,6}$) hept-3-yl)3-pentyn-2-one or tricyclene-9-butynone or 1,7-dimethyl-7-(1-pent-2-yn-4-only) nortricyclene | 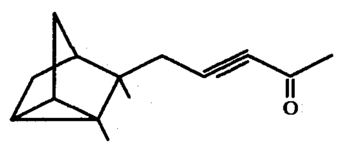 | Green, sweet, woody (sandal) aroma. |
| 5-(2,3-dimethyl tricyclo(2.2.1.0$^{2,6}$) hept-3-yl)3-pentan-2-one or tricyclene-9-butanone or 1,7-dimethyl-7-(1-pentan-4-onyl) nortricyclene | 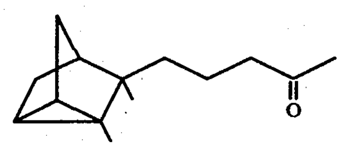 | Green, pumkin-like, sandalwood-oily aroma. |

One of the processes of our invention capable of yielding compound I, above, is a process for preparing a novel genus of tricyclic ketones having the structure:

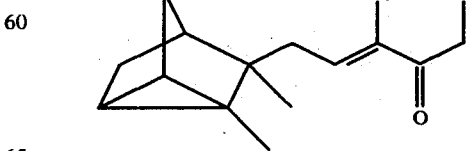

comprising the steps of:
i. Reacting a π-halotricyclene having the structure:

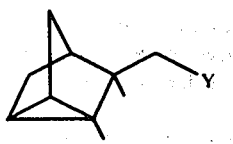

with an alkali metal cyanide in the presence of an inert solvent thereby forming a nitrile having the structure:

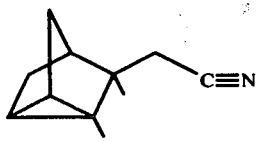

ii. Reacting the thus formed nitrile with diisobutyl aluminum hydride thus forming a nortricycloekasantalal having the structure:

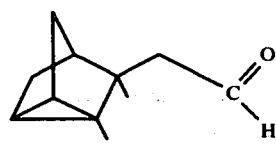

iii. Reacting the thus formed nortricycloekasantalal with a ketone having the structure:

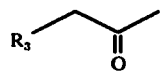

in the presence of a base selected from the group consisting of alkali metal hydroxides and alkaline earth metal hydroxides thus forming a tricyclic-alpha, beta-ketone having the structure:

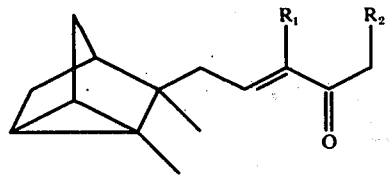

wherein Y is halogen selected from the group consisting of bromo, chloro and iode; $R_3$ is selected from the group consisting of hydrogen and methyl; and wherein $R_1$ and $R_2$ are each selected from the group consisting of hydrogen and methyl, provided that least one of $R_1$ or $R_2$ is hydrogen.

This process may optionally include the additional step (iii) of reacting with hydrogen, in the presence of a hydrogenation catalyst, the compound having the structure:

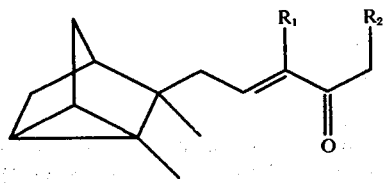

thereby forming a compound having the structure:

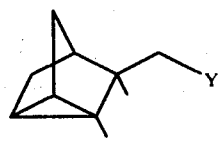

wherein $R_1$ and $R_2$ are each selected from the group consisting of hydrogen and methyl provided that at least one of $R_1$ or $R_2$ is hydrogen, in the event that it is desired to prepare compounds such as III, above.

The preparation of π-cyanotricyclene is carried out by reacting an alkali metal cyanide with a π-halo tricyclene having the generic formula:

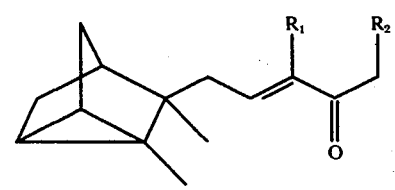

wherein Y is a halogen selected from the group consisting of chloro, bromo and iodo. Examples of alkali metal cyanide useful in the reaction are sodium cyanide and potassium cyanide. The reaction is carried out in an inert solvent such as dimethyl sulfoxide at a temperature in the range of from 80° up to 100° C; preferably 90° C. The mole ratio of alkali metal cyanide to π-halo tricyclene is from 10:1 up to 20:1 with a mole ratio of 15:1 being preferred.

The formation of nortricycloekasantalal is carried out by means of reduction of π-cyanotricyclene using such reducing reagents as diisobutyl aluminum hydride preferably premixed with inert solvent such as hexane. The reaction is carried out in an inert solvent such as hexane or cyclohexane in order to facilitate control of the reaction. The reaction temperature is preferably in the range of from about 40° up to 80° C with a temperature of about 55° C being preferred. The mole ratio of reduction reagent: π-cyanotricyclene is about 1:1 with the reduction reagent being in slight excess.

The genus of compounds having the structure:

is prepared by reacting the nortricycloekasantalal with a ketone having the structure:

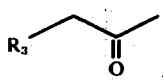

wherein $R_1$, $R_2$ and $R_3$ are each hydrogen or methyl with the proviso that at least one of $R_1$ or $R_2$ be hydrogen. Where $R_3$ is hydrogen, both $R_1$ and $R_2$ are hydrogen as is the case when the ketone used is acetone. When $R_3$ is methyl, a mixture of two compounds is produced: one where $R_1$ is methyl and the other where $R_2$ is methyl. This mixture can be easily separated by means of fractional distillation, thereby creating two sandalwood oil aroma-imparting components. The reaction is a standard "Aldol Condensation" type reaction which is carried out in the presence of a base which is either an alkali metal hydroxide such as lithium hydroxide, sodium hydroxide or potassium hydroxide or an alkaline earth metal hydroxide such as barium hydroxide or calcium hydroxide. A type of apparatus useful for carrying out the reaction when using an alkaline earth metal hydroxide is a "Soxhlet" apparatus; since the alkaline earth metal hydroxide is only very slightly soluble in the reaction medium.

The temperature of Aldol Condensation reaction is preferably in the range of from 25° up to 50° C with a temperature of about 35° C being preferred. The mole ratio of ketone:nortricycloekasantalal is preferably in the range of from 5:1 up to 15:1 with a ratio of about 7:1 being preferred. The quantity of base used in the reaction is preferably about 10% of the weight of ketone used; but quantities of base which are as low as 5% of the weight of ketone or as high as 20% of the weight or ketone may be used without creating an adverse effect on the yield of product. Quantities of base lower than 5% by weight of ketone will cause the time of reaction to be unduly lengthened. Quantities of base in excess of 20% will not have any beneficial effect on rate of reaction of yield of product; and will cause an excessive amount of by-products to be formed.

The hydrogenation of the genus of compounds having the structure:

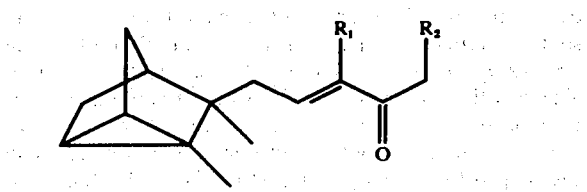

to form a second genus of compounds represented by the structure:

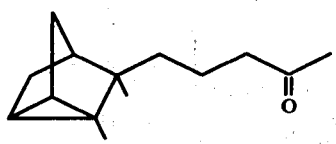

is carried out with hydrogen in the presence of a catalyst such as palladium, platinum, nickel or other suitable hydrogenation catalyst. Preferred catalysts are palladium on carbon and Raney nickel.

The reaction temperature may be from 20°–220° C with a temperature range of 20°–50° C being preferred. The reaction is preferably carried out at superatmospheric pressures and pressures in the range of 1–150 atmospheres are suitable. Preferred pressures range from 10–20 atmospheres.

A second of the processes capable of yielding compound II, above, is a process for preparing a tricyclic compound having the structure:

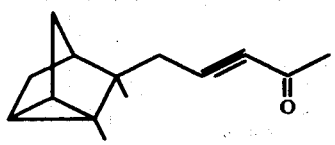

comprising the steps of:

i. Reacting a π-halo tricyclene having the structure:

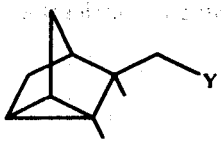

with acetylene lithium having the structure:

HC≡CLi thus forming 1,7-dimethyl-(1-prop-2-ynyl) nortricyclene having the structure:

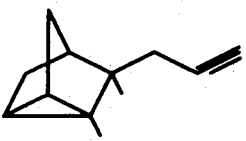

ii. Reacting the thus formed 1,7-dimethyl-(1-prop-2-ynyl) nortricyclene with $R_4Li$ to form 1,7-dimethyl-(1-prop-2-ynyl) nortricyclene lithium having the structure:

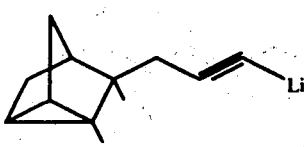

iii. Reacting the thus formed 1,7-dimethyl-(1-prop-2-ynyl) nortricyclene lithium with acetaldehyde in the presence of an inert solvent thus forming a tricyclic secondary alpha, beta alkynol having the structure:

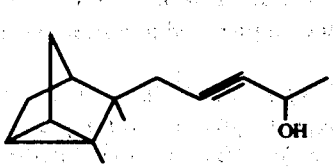

iv. Oxidizing the thus-formed tricyclic secondary alpha, beta alkynol with an alkali metal dichromate in acid solution thus forming a tricyclic alkynyl ketone having the structure:

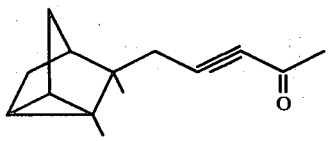

wherein Y is bromo, chloro or iodo, and $R_4$ is selected from the group consisting of phenyl and lower alkyl.

The first step of reacting a $\pi$-halo tricyclene having the structure:

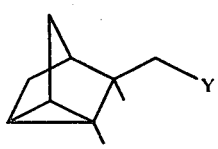

with acetylene lithium having the structure:

HC≡CLi to form 1,7-dimethyl-(1-prop-2-ynyl) nortricyclene having the structure:

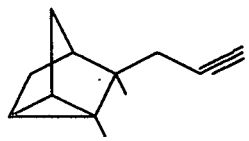

is preferably carried out in an inert solvent such as dimethyl sulfoxide. The lithium acetylide reactant is preferably added to the reaction mass in the form of a lithium acetylide - alkylene diamine complex (e.g., ethylene diamine complex) to facilitate control of the reaction. Y is a halogen moiety; either chloro, bromo or iodo. Preferably, the mole ratio of lithium acetylide: halo-tricyclene is about 2:1 but mole ratios of 1.1:1 up to 3:1 are suitable. The temperature of reaction may be in the range of 10° up to 80° C with room temperature being the preferred reaction temperature. The thus formed 1,7-dimethyl-(1-prop-2-ynyl) nortricyclene is then reacted with $R_4Li$ to form 1,7-dimethyl-(1-prop-2-ynyl) nortricyclene lithium having the structure:

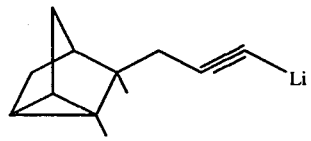

where R may be phenyl or alkyl. Thus, for example, suitable $R_4Li$ compounds are phenyl lithium, n-butyl lithium or t-butyl lithium.

The reaction is carried out in an inert solvent such as tetrahydrofuran. The preferred concentration range of reactant in solvent is from 0.05 up to 0.5 molar. The operable reaction temperature range is from 0° up to 50° C with room temperature being preferred and most convenient.

The thus-formed 1,7-dimethyl-(1-prop-2-ynyl) nortricyclene lithium is reacted with acetaldehyde in the presence of an inert solvent such as tetrahydrofuran or benzene or a mixture of these, or toluene thus forming a tricyclic secondary alkynol having the structure:

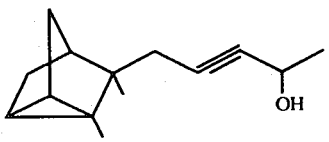

This reaction is preferably carried out at atmospheric pressure and at a temperature in the range of 10° up to 50° C; preferably and conveniently at room temperature.

The oxidation of the tricyclic secondary alkynol to the ketone is most preferably carried out using an alkali metal dichromate or a "chromic acid" oxidizing agent. Other oxidizing agents which may be used in the reaction in place of "chromic acid" are potassium permanganate, manganese dioxide, oxygen and air. It is most preferable to carry out this oxidation reaction in the presence of a solvent such as toluene although other solvents are also useful, such as pyridine, alpha-picoline, beta-picoline, delta-picoline, piperidine and ethanol amine.

When each of the aforementioned reactions is complete, the reaction mixture may be "worked-up" using routine purification procedures including the unit operations of extractions, cyrstallization, preparative chromatographic techniques, drying and/or distillation.

The $\pi$-tricyclene derivatives of our invention having a sweet, woody, oily and green sandalwoodlike notes can be used to contribute sandalwood aromas.

Although existant is relatively low proportions in sandalwood oil, compound (I) of our invention is considered to be at least one of the primary "sandalwood" aroma contributors of all of the constituents of sandalwood oil. Indeed, the relative strength of its aroma is several-fold that of any other known aroma contributors heretofore found in sandalwood oil; and this property is unexpected.

As olfactory agents several of the $\pi$-tricyclene derivatives of this invention can be formulated into or used as components of a "perfume composition".

The term "perfume composition" is used herein to mean a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh smelling materials.

In perfume compositions the individual component will contribute its particular olfactory characteristics, but the overall effect of the perfume composition will be the sum of the effect of each ingredient. Thus, $\pi$-tricyclene derivatives of this invention, can be used to alter the aroma characteristics of a perfume composition, for example, by highlighting or moderating the olfactory reaction contributed by another ingredient in the composition.

The amount of the π-tricyclene derivative of this invention which will be effective in perfume compositions depends on many factors, including the other ingredients, their amounts and the effects which are desired. It has been found that perfume compositions containing as little as 2 percent of the π-tricyclene derivative of this invention, or even less, can be used to impart a patchouli scent to soaps, cosmetics, and the other products. The amount employed can range up to 50% or higher and will depend on considerations of cost, nature of the end product, the effect desired on the finished product and particular fragrance sought.

The π-tricyclene derivative of this invention can be used alone or in a perfume composition as an olfactory component in detergents and soaps, space odorants and deodorants; perfumes; colognes; toilet waters; bath salts; hair preparations such as lacquers, brilliantines, pomades, and shampoos; cosmetic preparations such as creams, deodorants, hand lotions, and sun screens; powders such as talcs, dusting powders, face powder and the like. When used as an olfactory component of a perfumed article, as little as 0.01 percent of the π-tricyclene derivative will suffice to impart a key part of sandalwood aroma. Generally, no more than 0.5 percent is required.

In addition, the perfume composition can contain a vehicle or carrier for the π-tricyclene derivative alone or with other ingredients. The vehicle can be a liquid such as an alcohol such as ethanol, a glycol such as propylene glycol, or the like. The carrier can be an absorbent solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims. It is to be understood that unless otherwise stated all parts, proportions and percentages are by weight.

EXAMPLE I

Preparation of π-Cyanotriclene

Reaction:

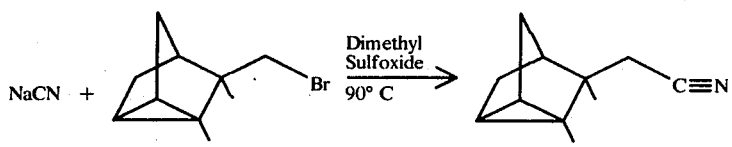

Into a 500 ml 3-neck, round bottom flask equipped with condenser, thermometer, mechanical stirrer, hot water heating bath and $N_2$ purge is charged 200 cc distilled dimethyl sulfoxide. 21.6 g (0.1 moles) of (-)-π-bromotricyclene is then added into the 500 ml flask containing the 200 ml of dimethyl sulfoxide. While stirring and purging with nitrogen 77.6 g (1.58 moles) of sodium cyanide is then added. Heating by means of the hot water bath to 90° C is then effected and the 90° C temperature is maintained for 22 hours. The reaction mass is then cooled to 40° C (below which temperature it becomes solidified) and 200 ml of water is added thereto. The aqueous phase is then extracted with five 100 ml portions of petroleum ether. The combined petroleum ether extracts are then washed with three 50 ml portions of saturated sodium chloride solution and dried over anhydrous $MgSO_4$. The dried extract is filtered and the solvents are evaporated yielding 21.2 g of crude product.

The crude product is distilled on a 2" rush-over column and collected three fractions. While distilling the condenser has to be heated as the pure nitrile solidifies.

| Fraction No. | Vapor Temp. | Distillation Data: Liquid Temp. | Weight of Fraction | Pressure |
|---|---|---|---|---|
| 1 | 30–52° C | 60–65° C | 0.1 g | 0.15 mm Hg |
| 2 | 55 | 70 | 1.7 | 0.15 |
| 3 | 70 | 90 | 9.0 | 0.10 |

NMR, mass spectral and IR analyses confirm that fractions 1 and 2 consist essentially of π-cyanotricyclene having the structure:

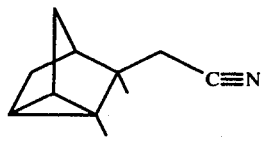

Analyses:
1. Mass spectral analysis in order of decreasing intensity:

m/e = 93, 121, 39, 27, 41.

2. The NMR spectrum is illustration in FIG. 1.
3. The IR spectrum is illustrated in FIG. 2.

EXAMPLE II

Preparation of Nortricycloekasantalal

Reaction:

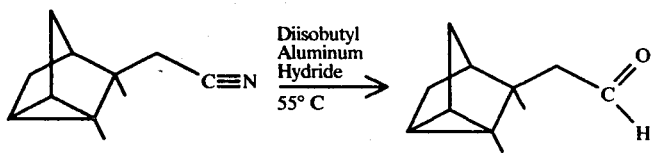

Into a 250 ml 3-neck, round bottom flask equipped with thermometer, condenser, mechanical stirrer, heating mantle, cooling bath (and mantle) and dropping funnel containing 75 ml hexane is charged 9 g (0.055 moles) of π-cyanotricyclene having the structure:

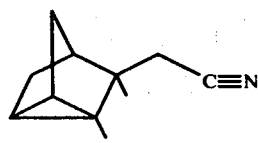

prepared according to Example I. While stirring and purging with $N_2$ slowly added 45 g (0.06 moles) diisobutyl aluminum hydride ("Dibal-H") (20% in hexane) over a period of ½ hours. The reaction temperature rises to 20° C and is heated to 55° C and maintained at that temperature for four hours. The reaction mixture is cooled to 5° C and 60 g of diethyl ether containing 0.5 ml of water is added slowly, followed by addition of 75 ml of 10% sulfuric acid. The upper organic phase is separated and washed with 15 ml of $NaHCO_3$ solution (saturated) and then with three 20 ml portions of saturated NaCl solution. The organic phase is then dried over anhydrous $MgSO_4$ and filtered. The solvent evaporated, yielding 16.2 g of crude aldehyde which is distilled on a 2" "rush-over" column and collected in four fractions. (Yield = 99.5%):

| Fraction No. | Liquid Temperature | Vapor Temperature | Pressure (mm Hg) | Weight of Fraction |
|---|---|---|---|---|
| 1 | 45–48° C | 30–35° C | 0.30 | 0.6 g |
| 2 | 51 | 43 | 0.20 | 3.3 |
| 3 | 65 | 41 | 0.15 | 4.6 |
| 4 | 85 | 46 | 0.15 | 0.8 |

NMR, mass spectral and IR analyses confirm that fractions 2 and 3 consist essentially of nortricycloekasantalal having the structure:

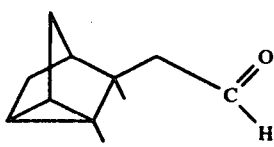

Analyses:
1. Mass spectral anslysis (in order of decreasing intensity):

m/e = 93/ 91, 105, 79, 120

Figure 4:
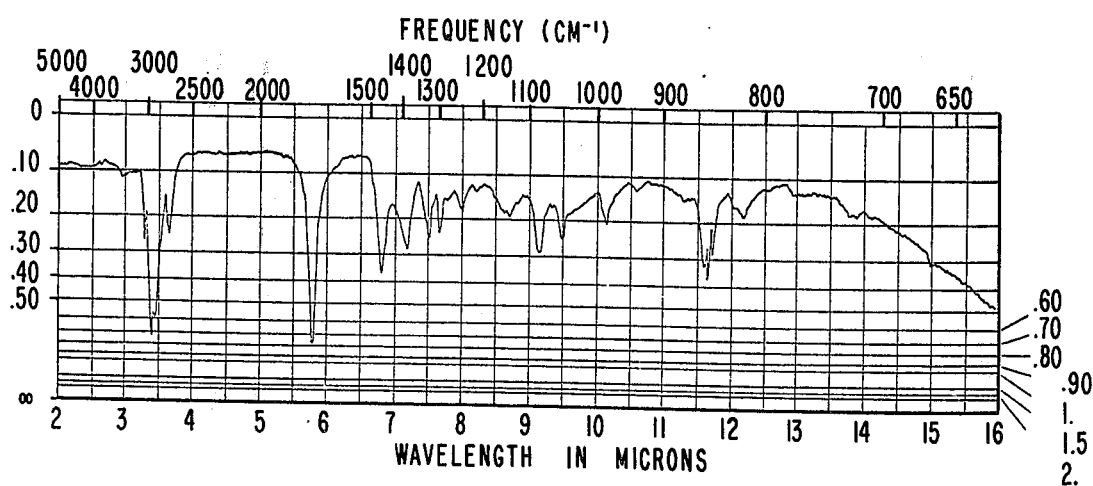

2. The NMR spectrum is illustrated in FIG. 3.
3. The IR spectrum is illustrated in FIG. 4.

EXAMPLE III

Preparation of 1,7-Dimethyl-7-(1-pent-2-en-4-onyl) Nortricyclene

Reaction:

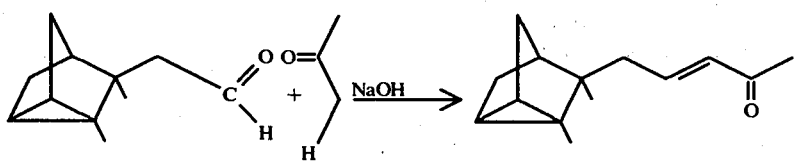

Into a 100 ml, 3-neck round bottom flask equipped with magnetic stirrer, thermometer and a heating mantle is placed 6 g (0.037 moles) of nortricycloekasantalal produced according to the process of Example II. A cold solution of 12.0 m. (0.23 moles) of acetone containing 1.2 g of NaOH and 3 ml of water is then added to the nortricycloekasantalal. The reaction mass is heated to 35° C and maintained at that temperature for 7 hours. The mass is then cooled and neutralized with 25 ml of aqueous HCl. The solvents are evaporated using a "roto vap" at about 70° C. The salts are then dissolved with water and the aqueous phase is extracted with five 30 ml portions of diethyl ether. The resulting ethereal solution is washed with three 20 ml portions of saturated NaCl solution, dried over anhydrous $MgSO_4$ and filtered. The solvents are evaporated yielding 7.2 g of crude product. The crude product is distilled on a 2" "rush-over" column (yield: 80%) yielding the following fractions:

| Fraction No. | Liquid Temperature | Vapor Temperature | Pressure (mm Hg) | Weight of Fraction |
|---|---|---|---|---|
| 1 | 60–116° C | 25–85° C | 0.2–0.3 | — |
| 2 | 119 | 93 | 0.2 | 1.2 g |
| 3 | 140 | 96 | 0.2 | 2.9 |
| 4 | 180 | 105 | 0.2 | 0.7 |

NMR, mass spectral and IR analyses confirm that fractions 2–4 consist essentially of 1,7-dimethyl-7 (1-pent-2-en-4-onyl) nortricyclene having the structure:

EXAMPLE IV

Preparation of 1,7-Dimethyl-7-(1-prop-2-ynyl) Nortricyclene

Reaction:

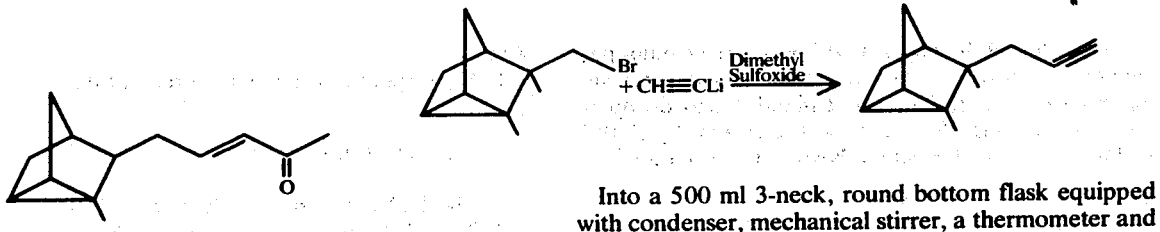

Analyses:
1. Mass spectral analysis (in order of decreasing intensity):

m/e = 121, 93, 43, 79, 91, 41

Figure 5:
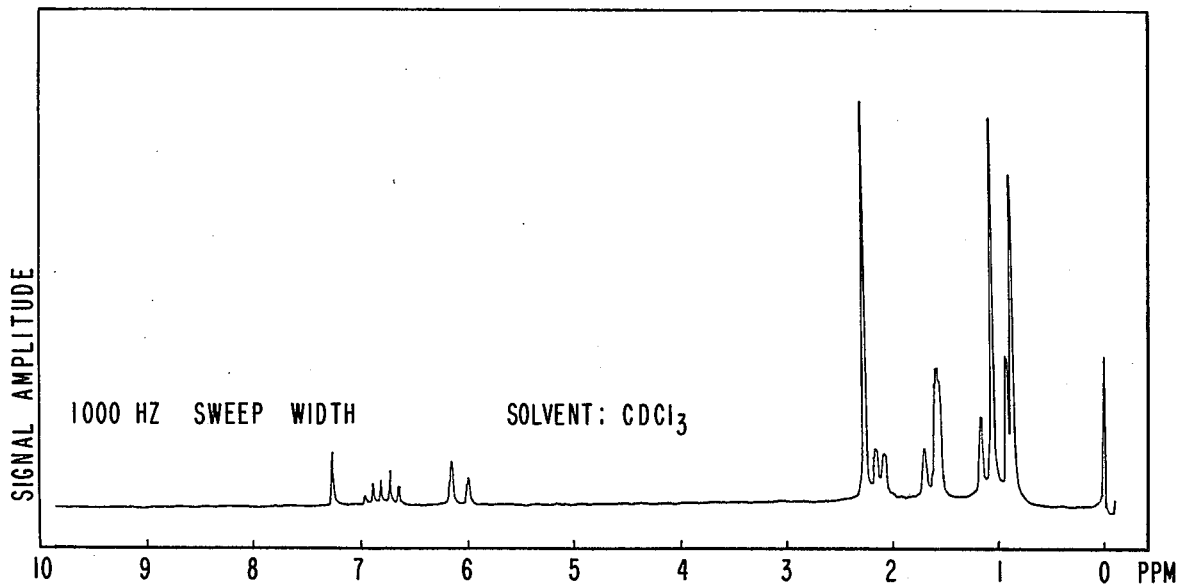
Figure 6:
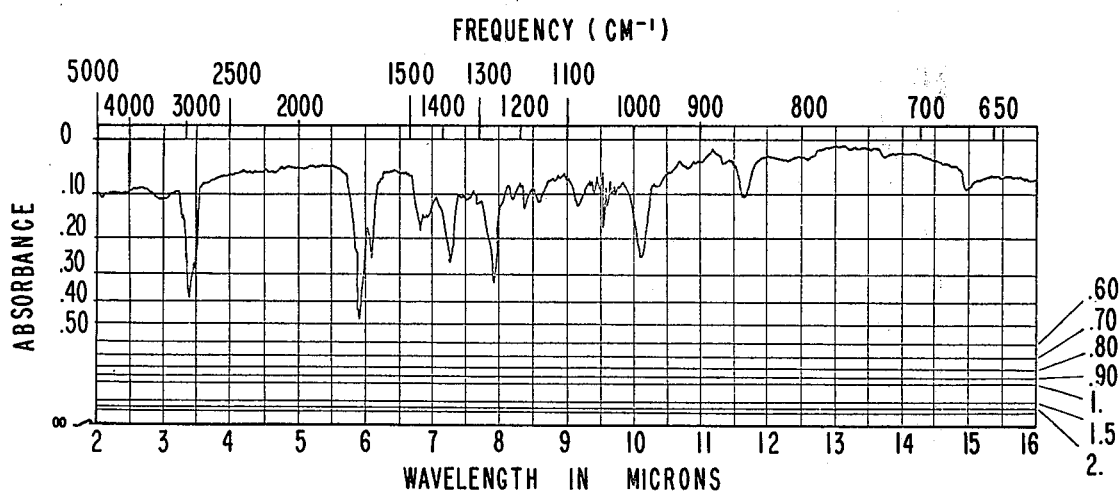

2. The NMR spectrum is illustrated in FIG. 5.
3. The IR spectrum is illustrated in FIG. 6.
4. The NMR analysis is as follows:

| Peak | | Interpretation |
|---|---|---|
| 0.86 ppm | (s) | $CH_3$—C— |
| 1.06 | (s) | $CH_3$—C— |
| 1.72–0.92 | | methylene and methine protons |
| 2.10 | (d) | $CH_2$—C=C—$\overset{O}{\overset{\|}{C}}$ |
| 2.28 | (s) | $CH_3$—$\overset{O}{\overset{\|}{C}}$— |
| 6.08 | | —C=C—$\overset{O}{\overset{\|}{C}}$ |
| 6.95–6.6 | | —$\overset{H}{\overset{\|}{C}}$=$\overset{}{\overset{}{C}}$—$\overset{}{\overset{\|}{C}}$—$\overset{O}{\overset{\|}{}}$ |

5. The infrared analysis is as follows:
   855 cm$^{-1}$
   985
   1088
   1160
   1190
   1260
   1370
   1440
   1460
   1640
   1675
   2850
   2950

Into a 500 ml 3-neck, round bottom flask equipped with condenser, mechanical stirrer, a thermometer and $N_2$ purge is placed 240 ml dimethyl sulfoxide. While stirring and purging with $N_2$ 48 g (0.48 moles) of lithium acetylide-ethylene diamine complex is added to the dimethyl sulfoxide. 38 g (0.24 moles) of (-)-π-bromotricyclene is then added and the reaction mass is stirred for 70 hours at room temperature. The reaction mass is then slowly added to 1600 ml of saturated ammonium chloride solution and extracted with six 200 ml portions of n-hexane. The hexane extracts are combined, washed with five 100 ml portions of saturated NaCl solution and dried over anydrous $MgSO_4$. The resulting hexane solution is filtered and the solvent evaporated to obtain 36.5 g of crude product. The crude product is distilled using a 2" "splash column" and collected in three fractions as follows:

| Fraction No. | Weight of Fraction | Liquid Temperature | Vapor Temperature | Pressure |
|---|---|---|---|---|
| 1 | 2.3 | 39–45° C | 26–31° C | 0.3 mm Hg |
| 2 | 11.8 | 60 | 34 | 0.2 |
| 3 | 4.3 | 100 | 35 | 0.3 |

Yield: 47%

NMR, mass spectral and IR analyses confirm that fractions 1–3 consist essentially of 1,7-dimethyl-7(1-prop-2-ynyl) nortricyclene having the structure:

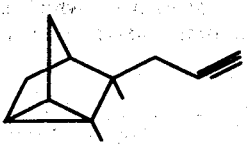

EXAMPLE V

Preparation of 1,7-Dimethyl-7-(1-(4'-hydroxy)pent-2-ynyl) Nortricyclene

Reaction:

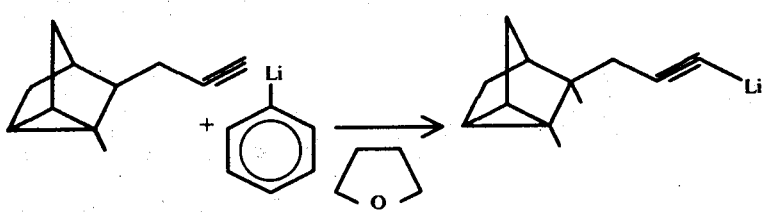

(i)

-continued

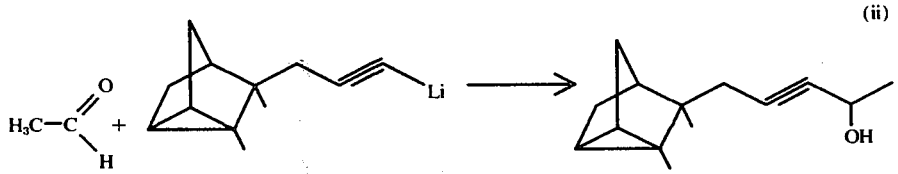

(ii)

Into a 3 liter round bottom flask equipped with mechanical stirrer, thermometer, condenser, addition funnel, a cooling bath and N₂ inlet is placed 350 ml distilled tetrahydrofuran. 9.0 g (0.055 moles) of 1,7-dimethyl-7-(1-prop-2-ynyl) nortricyclene prepared according to Example IV is then added to the tetrahydrofuran. The resulting mass is cooled to 0°-5° C and, while stirring and purging with N₂, 29 ml of a 2M phenyl lithium solution in benzene is added. The reaction mass is then stirred for 45 minutes and 3 g of acetaldehyde in 25 ml of tetrahydrofuran is added slowly. The reaction mass is then stirred at room temperature for a period of 16 hours. 100 ml of saturated NH₄Cl solution is then added and tetrahydrofuran is removed on a flash evaporator under reduced pressure and elevated temperature (50° C). To the residue 100 ml of saturated Nacl solution is added. The residue is then extracted with five 100 ml portions of diethyl ether. The combined ether solution is then washed with three 20 ml portions of saturated NaCl solution, dried over anhydrous MgSO₄ and filtered. The solvent is evaporated yielding 17 g of crude material.

The 17 g of crude product is then added to a chromatographic column containing 200 g of 5% deactivated silicic acid. The following table sets forth the various fractions removed from the column with the particular solvents used:

| Fraction No. | Solvent | Weight of Fraction |
| --- | --- | --- |
| 1 | 250 ml of 2% diethyl ether in isopentane | 7 g |
| 2 | 250 ml of 5% diethyl ether in isopentane | 2.5 g |
| 3 | 250 ml of 10% diethyl ether in isopentane | 0.3 g |
| 4 | 250 ml of 15% diethyl ether in isopentane | 2.0 g |
| 5 | 250 ml of 20% diethyl ether in isopentane | 0.9 g |
| 6 | 250 ml of diethyl ether | 0.8 g |

Fraction No. 4 weighing 2.0 g is analyzed using GLC apparatus (conditions: 5% Carbowax 20M column; 20' × ¼"). Peak 5 is determined by IR, NMR and mass spectral analyses to be a compound having the structure:

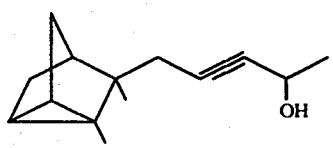

Fraction No. 4 is dissolved in 40 ml diethyl ether and washed with three 5 ml portions of 5% sodium hydroxide in order to remove the phenol. It is then washed with three 25 ml portions of saturated sodium chloride solution, dried over anhydrous magnesium sulfate and filtered. The solvent is evaporated yielding 1.5 g of crude product.

Analysis:
1. Mass spectral analysis (Parent Peak, then in order of decreasing intensity):

m/e = 204(M⁺); 41, 55, 39, 70, 93, 43, 121.

2. The NMR spectrum is illustrated in FIG. 7.
3. The IR spectrum is illustrated in FIG. 8.
4. The NMR analysis is as follows:

| Peak | | Interpretation |
| --- | --- | --- |
| 0.94 | (s) | CH₃—C— |
| 1.02 | (s) | CH₃—C— |
| 1.44 | (d) | CH₃—C̲H—C— <br> \| <br> O |
| 1.70–0.84 | | methylene and methine protons |
| 2.06 | | —CH₂—C≡C— |
| 4.6 | | C≡C—C̲H—O— |

5. The infrared analysis is as follows:
820 cm⁻¹
855
892
1005
1075
1160
1300
1317
1380
1460
2990
3310

EXAMPLE VI

Preparation of 1,7-Dimethyl-7-(1-pent-2-yn-4-onyl) Nortricyclene

Reaction:

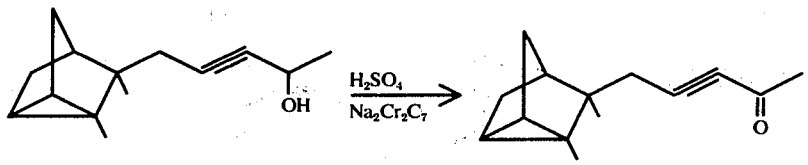

Procedure:

To a 100 ml 3-neck, round bottom flask equipped with stirrer, thermometer and $N_2$ inlet is added 30 ml of toluene and 1.8 g of the crude material, fraction 4, containing 1,7-dimethyl-7-(1-(4'-hydroxy)pent-2-ynyl) nortricyclene produced according to Example V. While stirring the mixture is cooled to 0°–5° C. A mixture of 1.5 g of $Na_2Cr_2O_7$ in 4 ml of water and 1.5 g of conc. $H_2SO_4$ is then added, and the reaction mass is stirred for a period of 3 hours. The resulting organic layer is separated and washed with two 25 ml portions of saturated sodium carbonate solution. The organic phase is then washed with three 20 ml portions of saturated NaCl solution, dried over anhydrous $MgSO_4$ and filtered. The solvent is evaporated yielding crude product weighing about 1.5 g.

The 1.5 g of crude product is placed in a chromatographic column containing 75 g of 5% deactivated silicic acid. The following table sets forth the various fractions removed from the column giving the particular solvents used for each fraction:

| Fraction No. | Solvent |
| --- | --- |
| 1 | 100 ml of 2% diethyl ether in isopentane |
| 2 | 100 ml of 2% diethyl ether in isopentane |
| 3 | 100 ml of 2% diethyl ether in isopentane |
| 4 | 100 ml of 2% diethyl ether in isopentane |
| 5 | 100 ml of 4% diethyl ether in isopentane |
| 6 | 100 ml of 4% diethyl ether in isopentane |
| 7 | 100 ml of 4% diethyl ether in isopentane |
| 8 | 100 ml of 4% diethyl ether in isopentane |
| 9 | 100 ml of 4% diethyl ether in isopentane |
| 10 | 100 ml of 4% diethyl ether in isopentane |
| 11 | 100 ml of 4% diethyl ether in isopentane |
| 12 | 100 ml of 4% diethyl ether in isopentane |
| 13 | 100 ml of 6% diethyl ether in isopentane |
| 14 | 100 ml of 6% diethyl ether in isopentane |
| 15 | 100 ml of 6% diethyl ether in isopentane |
| 16 | 100 ml of 6% diethyl ether in isopentane |
| 17 | 500 ml of 8% diethyl ether in isopentane |
| 18 | 500 ml of 10% diethyl ether in isopentane |

Fractions Nos. 10–12 are combined and evaporated. The components are then trapped using GLC apparatus (conditions: 5% Carbowax 20M column; 20' × ¼''). Peak No. 4 consists essentially of the compound having the structure:

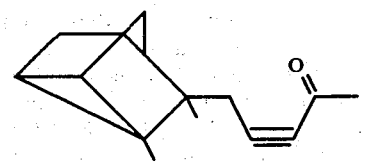

as confirmed by NMR, IR and mass spectral analyses. It has a green, sweet, sandalwood aroma.

Analysis:

1. Mass spectral analysis (parent peak, then in order of decreasing intensity:

$m/e = 202(M^+); 93, 43, 41, 39, 121, 55.$

2. The IR spectrum is illustrated in FIG. 9.

EXAMPLE VII

Preparation of 1,7-dimethyl-7-(1-pentan-4-onyl) Nortricyclene

Reaction:

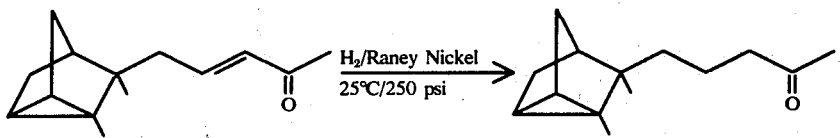

A Parr (2 L Bomb) pressure reaction apparatus equipped with a stirrer and connected to a hydrogen cylinder is charged with 1,7-dimethyl-7-(1-pent-2-en-4-onyl) nortricyclene prepared according to the procedure of Example III 500 g, isopropyl alcohol 250 g, Raney Nickel 25 g and the hydrogenation is carried out at 25° C under a pressure of 250 psi for 2 hours. The progress of the reaction is monitored by observing the disappearance of IR bands at 6.1 and 10.2 u and the shifting of the carbonyl absorption band from 5.9 to 5.8 u. The reaction mixture is filtered through Celite and the solvent is evaporated on a Rinco flask evaporator under house vacuum to obtain 490 g of crude material (yield = 98%).

NMR, IR and mass spectral analysis confirm the structure of the reaction product as being:

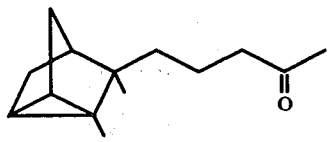

This material has a green, pumpkin like, sandalwood-oily-like aroma.

Analyses:
1. Mass spectral analysis (in decreasing order of intensity):

m/e = 121, 93, 206 (Molecular ion), 43, 107.

Figure 11:
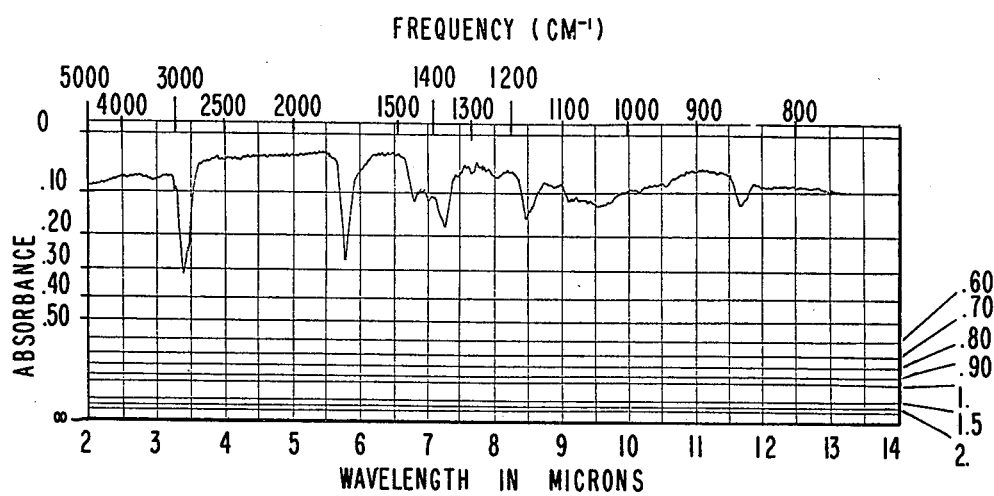

2. The NMR spectrum is illustrated in FIG. 10.
3. The IR spectrum is illustrated in FIG. 11.
4. The NMR analysis is as follows:

| Peak | | Interpretation | |
|---|---|---|---|
| 0.84 ppm | (s) | $CH_3$—C— | 6H |
| 1.50 | (s) | $CH_3$—C— | |
| 1.76–1.10 | (m) | Methylene and methine protons | 11H |
| 2.14 | (s) | $CH_3$—C=O | 3H |
| 2.41 | (t) | —$CH_2$—C=O | |

5. The infrared analysis is as follows:
   855 cm$^{-1}$
   1165
   1370
   1420
   1460
   1725
   2900
   2950

EXAMPLE VIII

Separation of Sandalwood Oil Components 200 g of sandalwood oil is admixed with 2 liters of diethyl ether. The resulting mixture is washed with three 50 ml portions of 10% sodium carbonate solution. The washings are combined and they are washed with five 50 ml portions of diethyl ether. The resulting ether washings are combined with the original washed ether solution and this combined diethyl ether solution is then washed with three 50 ml portions of 5% aqueous sodium hydroxide. The sodium hydroxide washings are re-extracted with five 50 ml portions of diethyl ether and these ether extracts are combined with the original ether solution and the combined ether solution is then extracted with three 50 ml portions of 4% hydrochloric acid. The extracted ether solution is then washed with 100 ml saturated sodium chloride solution followed by four 50 ml portions of water (until the water washing no longer shows an acid pH). The ether solution is then dried over anhydrous magnesium sulfate filtered and evaporated to yield 197.8 g of crude product.

a. 140 g of the material is then distilled on a spinning band column operating at a reflux ratio of 100:1 and 6 fractions are collected.

| Fraction No. | Vapor Temperature | Liquid Temperature | Pressure (mm Hg) | Weight of Fraction |
|---|---|---|---|---|
| 1 | 70–72° C | 152–156° C | 0.40 | 1.8 |
| 2 | 74 | 156 | 0.45 | 1.9 |
| 3 | 80 | 160 | 0.6 | 1.8 |
| 4 | 92 | 160 | 0.6 | 1.9 |
| 5 | 93 | 161 | 0.6 | 2.6 |
| 6 | 90 | 161 | 0.6 | 2.3 |

Fractions 1–4 are combined.

b. 55 g of the above material are also distilled on a spinning band column yielding 5 fractions as follows:

| Fraction No. | Vapor Temperature | Liquid Temperature | Pressure (mm Hg) | Weight of Fraction |
|---|---|---|---|---|
| 1 | 70–74° C | 158–160° C | 0.5–0.6 | 2.1 |
| 2 | 78 | 160 | 0.4 | 1.7 |
| 3 | 98 | 160 | 0.6 | 1.7 |
| 4 | 103 | 160 | 0.6 | 1.6 |
| 5 | 105 | 158 | 0.6 | 1.3 |

Fractions 1–3 are combined.

The combined distillates of distillation operations (a) and (b), supra, are placed in a chromatographic column containing 400 g of 5% deactivated silicic acid. Initially, two fractions are removed:

i. The first fraction contains hydrocarbon and is removed with 1.5 liters of isopentane;

ii. The second fraction contains oxygenated material and is removed with 1.5 liters of diethyl ether.

The oxygenated material is then placed in a Carbowax column containing 130 g of 5% deactivated silicic acid. The following table sets forth the various fractions removed from the column giving the particular solvents used for each fraction:

| Fraction No. | Solvent |
|---|---|
| 1 | 350 ml of 1% diethyl ether in isopentane |
| 2 | 150 ml of 1% diethyl ether in isopentane |
| 3 | 100 ml of 2% diethyl ether in isopentane |
| 4 | 100 ml of 2% diethyl ether in isopentane |
| 5 | 100 ml of 2% diethyl ether in isopentane |
| 6 | 100 ml of 2% diethyl ether in isopentane |
| 7 | 50 ml of 2% diethyl ether in isopentane |
| 8 | 50 ml of 2% diethyl ether in isopentane |
| 9 | 50 ml of 2% diethyl ether in isopentane |
| 10 | 50 ml of 2% diethyl ether in isopentane |
| 11 | 25 ml of 2% diethyl ether in isopentane |
| 12 | 25 ml of 2% diethyl ether in isopentane |
| 13 | 25 ml of 2% diethyl ether in isopentane |
| 14 | 25 ml of 2% diethyl ether in isopentane |
| 15 | 25 ml of 2% diethyl ether in isopentane |
| 16 | 25 ml of 2% diethyl ether in isopentane |
| 17 | 25 ml of 2% diethyl ether in isopentane |
| 18 | 25 ml of 2% diethyl ether in isopentane |
| 19 | 25 ml of 2% diethyl ether in isopentane |
| 20 | 25 ml of 2% diethyl |

-continued

| Fraction No. | Solvent |
|---|---|
| 21 | 25 ml of 2% diethyl ether in isopentane |
| 22 | 25 ml of 2% diethyl ether in isopentane |
| 23 | 25 ml of 2% diethyl ether in isopentane |
| 24 | 25 ml of 2% diethyl ether in isopentane |
| 25 | 25 ml of 2% diethyl ether in isopentane |
| 26 | 25 ml of 2% diethyl ether in isopentane |
| 27 | 25 ml of 2% diethyl ether in isopentane |
| 28 | 25 ml of 2% diethyl ether in isopentane |
| 29 | 25 ml of 3% diethyl ether in isopentane |
| 30 | 25 ml of 3% diethyl ether in isopentane |
| 31 | 25 ml of 3% diethyl ether in isopentane |
| 32 | 25 ml of 3% diethyl ether in isopentane |
| 33 | 25 ml of 3% diethyl ether in isopentane |
| 34 | 25 ml of 3% diethyl ether in isopentane |
| 35 | 25 ml of 3% diethyl ether in isopentane |
| 36 | 25 ml of 3% diethyl ether in isopentane |
| 37 | 25 ml of 3% diethyl ether in isopentane |
| 38 | 25 ml of 3% diethyl ether in isopentane |
| 39 | 25 ml of 3% diethyl ether in isopentane |
| 40 | 25 ml of 3% diethyl ether in isopentane |
| 41 | 25 ml of 3% diethyl ether in isopentane |
| 42 | 25 ml of 4% diethyl ether in isopentane |
| 43 | 25 ml of 4% diethyl ether in isopentane |
| 44 | 25 ml of 4% diethyl ether in isopentane |
| 45 | 25 ml of 4% diethyl ether in isopentane |
| 46 | 25 ml of 4% diethyl ether in isopentane |
| 47 | 25 ml of 4% diethyl ether in isopentane |
| 48 | 25 ml of 4% diethyl ether in isopentane |
| 49 | 25 ml of 4% diethyl ether in isopentane |
| 50 | 25 ml of 4% diethyl ether in isopentane |
| 51 | 25 ml of 4% diethyl ether in isopentane |
| 52 | 25 ml of 4% diethyl ether in isopentane |
| 53 | 25 ml of 4% diethyl ether in isopentane |
| 54 | 25 ml of 4% diethyl ether in isopentane |
| 55 | 25 ml of 4% diethyl ether in isopentane |
| 56 | 25 ml of 4% diethyl ether in isopentane |
| 57 | 25 ml of 4% diethyl ether in isopentane |
| 58 | 25 ml of 5% diethyl ether in isopentane |
| 59 | 25 ml of 5% diethyl ether in isopentane |
| 60 | 25 ml of 5% diethyl ether in isopentane |
| 61 | 25 ml of 5% diethyl ether in isopentane |
| 62 | 25 ml of 5% diethyl ether in isopentane |
| 63 | 25 ml of 5% diethyl ether in isopentane |
| 64 | 25 ml of 5% diethyl ether in isopentane |
| 65 | 25 ml of 5% diethyl ether in isopentane |

-continued

| Fraction No. | Solvent |
|---|---|
| 66 | 25 ml of 5% diethyl ether in isopentane |
| 67 | 25 ml of 5% diethyl ether in isopentane |
| 68 | 25 ml of 5% diethyl ether in isopentane |
| 69 | 25 ml of 5% diethyl ether in isopentane |
| 70 | 25 ml of 5% diethyl ether in isopentane |
| 71 | 25 ml of 5% diethyl ether in isopentane |
| 72 | 25 ml of 5% diethyl ether in isopentane |
| 73 | 25 ml of 6% diethyl ether in isopentane |
| 74 | 25 ml of 6% diethyl ether in isopentane |
| 75 | 25 ml of 6% diethyl ether in isopentane |
| 76 | 25 ml of 6% diethyl ether in isopentane |
| 77 | 25 ml of 6% diethyl ether in isopentane |
| 78 | 25 ml of 6% diethyl ether in isopentane |
| 79 | 25 ml of 6% diethyl ether in isopentane |
| 80 | 25 ml of 6% diethyl ether in isopentane |
| 81 | 25 ml of 6% diethyl ether in isopentane |
| 82 | 25 ml of 6% diethyl ether in isopentane |
| 83 | 25 ml of 6% diethyl ether in isopentane |
| 84 | 25 ml of 6% diethyl ether in isopentane |
| 85 | 25 ml of 6% diethyl ether in isopentane |
| 86 | 25 ml of 6% diethyl ether in isopentane |
| 87 | 25 ml of 6% diethyl ether in isopentane |
| 88 | 25 ml of 6% diethyl ether in isopentane |
| 89 | 25 ml of 6% diethyl ether in isopentane |
| 90 | 25 ml of 6% diethyl ether in isopentane |
| 91 | 25 ml of 6% diethyl ether in isopentane |
| 92 | 25 ml of 7% diethyl ether in isopentane |
| 93 | 25 ml of 7% diethyl ether in isopentane |
| 94 | 25 ml of 7% diethyl ether in isopentane |
| 95 | 25 ml of 7% diethyl ether in isopentane |
| 96 | 25 ml of 7% diethyl ether in isopentane |
| 97 | 25 ml of 7% diethyl ether in isopentane |
| 98 | 25 ml of 7% diethyl ether in isopentane |
| 99 | 25 ml of 7% diethyl ether in isopentane |
| 100 | 25 ml of 7% diethyl ether in isopentane |
| 101 | 25 ml of 7% diethyl ether in isopentane |
| 102 | 25 ml of 7% diethyl ether in isopentane |
| 103 | 25 ml of 7% diethyl ether in isopentane |
| 104 | 25 ml of 7% diethyl ether in isopentane |
| 105 | 25 ml of 7% diethyl ether in isopentane |
| 106 | 25 ml of 10% diethyl ether in isopentane |
| 107 | 25 ml of 10% diethyl ether in isopentane |
| 108 | 25 ml of 10% diethyl ether in isopentane |
| 109 | 25 ml of 10% diethyl ether in isopentane |
| 110 | 25 ml of 10% diethyl ether in isopentane |
| 111 | 25 ml of 10% diethyl |

-continued

| Fraction No. | Solvent |
| --- | --- |
| 112 | 25 ml of 10% diethyl ether in isopentane |
| 113 | 25 ml of 10% diethyl ether in isopentane |
| 114 | 25 ml of 10% diethyl ether in isopentane |
| 115 | 25 ml of 10% diethyl ether in isopentane |
| 116 | 25 ml of 10% diethyl ether in isopentane |
| 117 | 25 ml of 10% diethyl ether in isopentane |
| 118 | 25 ml of 10% diethyl ether in isopentane |
| 119 | 25 ml of 10% diethyl ether in isopentane |
| 120 | 25 ml of 15% diethyl ether in isopentane |
| 121 | 25 ml of 15% diethyl ether in isopentane |
| 122 | 25 ml of 15% diethyl ether in isopentane |
| 123 | 25 ml of 15% diethyl ether in isopentane |
| 124 | 25 ml of 15% diethyl ether in isopentane |
| 125 | 25 ml of 15% diethyl ether in isopentane |
| 126 | 25 ml of 15% diethyl ether in isopentane |
| 127 | 25 ml of 15% diethyl ether in isopentane |
| 128 | 25 ml of 15% diethyl ether in isopentane |
| 129 | 25 ml of 15% diethyl ether in isopentane |
| 130 | 25 ml of 15% diethyl ether in isopentane |
| 131 | 100 ml of 20% diethyl ether in isopentane |
| 132 | 100 ml of 20% diethyl ether in isopentane |
| 133 | 100 ml of 20% diethyl ether in isopentane |
| 134 | 50 ml of 30% diethyl ether in isopentane |
| 135 | 500 ml of 40% diethyl ether in isopentane |
| 136 | 250 ml of 50% diethyl ether in isopentane |
| 137 | 750 ml of 100% diethyl ether in isopentane |

The solvent is evaporated from fractions 41 and fraction 41 is separated using GLC (conditions: 5% Carbowax 20M column; 20' × ¼"). IR, NMR and mass spectral analyses of the compound in GLC peak 7c yields the information that the structure of the compound in Peak 7c is:

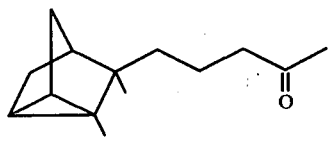

Analysis:

NMR, IR and mass spectral analyses are identical to those of the same compound produced in Example VII. The NMR and IR spectra are illustrated respectively in FIGS. 10 and 11.

The solvent is evaporated from fraction 63 and this material is trapped out using GLC apparatus (conditions: 5% carbowax 20M column; 20' × ¼"). Peak 3a is analyzed using IR, NMR and mass spectral analyses and these analyses yield information confirming the structure of the compound of Peak 3a to be:

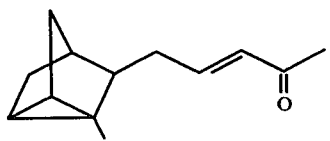

Analysis:

NMR, IR and mass spectral analyses are identical to those of the same compound produced in Example III. The NMR and IR spectra are illustrated respectively in FIGS. 5 and 6.

EXAMPLE IX

Sandal Perfume Formulation

The following mixture is prepared:

| Ingredients | Parts by Weight |
| --- | --- |
| 1',2',3',4',5',6',7',8'-octahydro-2',3',8',8'-tetramethyl-2'-acetonaphthone isomer mixture produced according to the process of Example VII of Application for U.S. Letters Patent No. 434,948 filed on January 21, 1974 | 540 |
| Cedrenal - (A tricyclic sesquiterpinic aldehyde derived from cedrene, having the structure: ![structure] produced according to the process of U.S. Patent Application 260,537 filed on June 7, 1972 (corresponding to published Dutch Appln. 7,307,849 laid open for public inspection on December 11, 1973) | 90 |
| Eugenol (1% in ethyl alcohol) | 54 |
| 2,5,5-trimethyl acetyl cycloheptane produced according to Example I of U.S. Patent Application 349,180 filed on April 9, 1973 | 180 |
| Borneol (1% in ethyl alcohol) | 18 |
| Hexahydro-4,7-methanoindane-2-carboxaldehyde | 18 |
| Tricyclene-9-butenone having the structure: ![structure] produced according to Example III | 100 |

The tricyclene-9-butenone imparts the green, woody, slightly sweaty note of sandal to the formulation.

EXAMPLE X

Preparation of a Soap Composition

A total of 100 g of soap chips produced from unperfumed sodium base toilet soap made from tallow and coconut oil are mixed with 1 g of the perfume composition set forth in Example IX until a substantially homogeneous composition is obtained. The soap composition manifests a characteristic "sandal cologne" aroma having

EXAMPLE XI

Preparation of a Soap Composition

A total of 100 g of soap chips produced from unperfumed sodium base toilet soap made from tallow and coconut oil is mixed with 1 g of tricyclene-9-butenone produced according to Example III until a substantially homogeneous composition is obtained. The soap composition manifests a green, woody, sandalwood oil character.

EXAMPLE XII

Preparation of a Detergent Composition

A total of 100 g of a detergent powder sold under a trademark "RINSO" are mixed with 0.15 g of a perfume composition containing the mixture obtained in Example IX until a substantially homogeneous composition having a "sandal cologne" fragrance with green, woody and sweaty notes is obtained.

EXAMPLE XIII

Preparation of a Cosmetic Base

A cosmetic powder is prepared by mixing 100 g of talcum powder with 0.25 g of the perfume composition of Example IX in a ball mill. A second cosmetic powder is similarly prepared except that the mixture produced in Example IX is replaced with the product produced in Example III. The cosmetic powder containing the material of Example IX has a "sandal cologne" fragrance with a green, woody, sweaty character. The cosmetic powder produced using this material of Example III also has a sandalwood aroma with sweet, woody, oily, sweaty, amber and orrisey notes.

EXAMPLE XIV

Liquid Detergent Containing Tricyclene-9-Butenone

Concentrated liquid detergents with a sandalwood-like odor containing 0.2, 0.5 and 1.2% of the product produced in accordance with the process of Example III are prepared by adding the appropriate quantity of tricyclene-9-butenone to the liquid detergent known as P-87. The sandalwood aroma of the liquid detergent increases with increasing concentration of the tricyclene-9-butenone of this invention.

EXAMPLE XV

Preparation of Cologne and Handkerchief Perfume

The composition of Example IX is incorporated in a cologne having a concentration of 2.5 in 85% aqueous ethanol; and into a handkerchief perfume in a concentration of 20% (in 95% ethanol). The use of the composition of Example IX affords a distinct and definite "sandal cologne" aroma having a warm sandalwood-like character to the handkerchief perfume and to the cologne.

EXAMPLE XVI

Cologne and Handkerchief Perfume

The tricyclene-9-butenone produced by the process of Example III is incorporated into a cologne having a concentration of 2.5 in 85% ethanol; and into a handkerchief perfume in a concentration of 10% (in 95% ethanol). The tricyclene-9-butenone produced in Example III affords a distinct and definite sandalwood aroma with sweet, woody, oily, sweaty, amber and orrisey notes to the handkerchief perfume and to the cologne.

EXAMPLE XVII

Sandal Perfume Formulation

The following mixture is prepared:

| Ingredients | Parts by Weight |
| --- | --- |
| 1',2',3',4',5',6',7',8'-octahydro-2',3',8',8'-tetramethyl-2'-acetonaphthone isomer mixture produced according to the process of Example VII of Application for U.S. Letters Patent No. 434,948 filed on January 21, 1974 | 540 |
| Cedrenal - (A tricyclic sesquiterpinic aldehyde derived from cedrene, having the structure: <br><br> produced according to the process of U.S. Patent Application 260,537 filed on June 7, 1972 (corresponding to published Dutch Appln. 7,307,849 laid open for public inspection on December 11, 1973) | 90 |
| Eugenol (1% in ethyl alcohol) | 54 |
| 2,5,5-trimethyl acetyl cycloheptane produced according to Example I of U.S. Patent Applicaton 349,180 filed on April 9, 1973 | 180 |
| Borneol (1% in ethyl alcohol) | 18 |
| Hexahydro-4,7-methanoindane-2-carboxaldehyde | 18 |
| Tricyclene-9-butynone having the structure: <br><br> produced according to Example VI | 100 |

The tricyclene-9-butynone imparts the green, woody, sweet note of sandal to the formulation.

EXAMPLE XVIII

Preparation of a Soap Composition

A total of 100 g of soap chips produced from unperfumed sodium base toilet soap made from tallow and coconut oil are mixed with 1 g of the perfume composition set forth in Example XVII until a substantially homogeneous composition is obtained. The soap composition manifests a characteristic "sandal cologne" aroma having green, sweet and woody notes.

EXAMPLE XIX

Preparation of a Soap Composition

A total of 100 g of soap chips produced from unperfumed sodium base toilet soap made from tallow and coconut oil is mixed with 1 g of tricyclene-9-butynone produced according to Example VI until a substantially homogeneous composition is obtained. The soap composition manifests a sandalwood-like character with green, woody and sweet notes.

EXAMPLE XX

Preparation of a Detergent Composition

A total of 100 g of a detergent powder sold under the trademark "RINSO" are mixed with 0.15 g of a perfume composition containing the mixture obtained in Example XVII until a substantially homogeneous composition having a "sandal cologne" fragrance with green, sweet and woody notes is obtained.

EXAMPLE XXI

Preparation of a Cosmetic Base

A cosmetic powder is prepared by mixing 100 g of talcum powder with 0.25 g of the perfume composition of Example XVII in a ball mill. A second cosmetic powder is similarly prepared except that the mixture produced in Example XVII is replaced with the product produced in Example VI. The cosmetic powder containing the material of Example XVII has a "sandal cologne" fragrance with a green, sweet, woody character. The cosmetic powder produced using the material of Example VI has a sandalwood-like aroma with green, sweet, woody notes.

EXAMPLE XXII

Liquid Detergent Containing Tricyclene-9-Butynone

Concentrated liquid detergents with a sandalwood like odor containing 0.2, 0.5 and 1.2% of the product produced in accordance with the process of Example VI are prepared by adding the appropriate quantity of tricyclene-9-butynone to the liquid detergent known as P-87. The sandalwood aroma of the liquid detergent increases with increasing concentration of the tricyclene-9-butynone of this invention.

EXAMPLE XXIII

Preparation of Cologne and Handkerchief Perfume

The composition of Example XVII is incorporated in a cologne having a concentration of 2.5% in 85% aqueous ethanol; and into a handkerchief perfume in a concentration of 20% (in 95 ethanol). The use of the composition of Example XVII affords a distinct and definite "sandal cologne" aroma having a warm sandalwood-like character to the handkerchief perfume and to the cologne.

EXAMPLE XXIV

Cologne and Handkerchief Perfume

The tricyclene-9-butynone produced by the process of Example VI is incorporated into a cologne having a concentration of 2.5% in 85% ethanol; and into a handkerchief perfume in a concentration of 10% (in 95% ethanol). The tricyclene-9-butynone produced in Example VI affords a distinct and definite sandalwood-like aroma with green, woody and sweet notes to the handkerchief perfume and to the cologne.

EXAMPLE XXV

Sandal Perfume Formulation

The following mixture is prepared:

| Ingredients | Parts by Weight |
|---|---|
| 1',2',3',4',5',6',7',8'-octahydro-2",3',8',8'-tetramethyl-2'-acetonaphthone isomer mixture produced according to the process of Example VII of Application for U.S. Letters Patent No. 434,948 filed on January 21, 1974 | 540 |
| Cedrenal - (A tricyclic sesquiterpinic aldehyde derived from cedrene, having the structure: [structure shown] produced according to the process of U.S. Patent Application 260,537 filed on June 7, 1972 (corresponding to published Dutch Appln. 7,307,849 laid open for public inspection on December 11, 1973) | 90 |
| Eugenol (1% in ethyl alcohol) | 54 |
| 2,5,5-trimethyl acetyl cylco-heptane produced according to Example I of U.S. Patent Application 349,180 filed on April 9, 1973 | 180 |
| Borneol (1% in ethyl alcohol) | 18 |
| Hexahydro-4,7-methanoindane-2-carboxaldehyde | 18 |
| Tricyclene-9-butanone having the structure: [structure shown] produced according to Example VII | 100 |

The tricyclene-9-butanone imparts the green, pumpkin-like and oily notes of sandal to the formulation.

EXAMPLE XXVI

Preparation of a Soap Composition

A total of 100 g of soap chips produced from unperfumed sodium base toilet soap made from tallow and coconut oil are mixed with 1 g of the perfume composition set forth in Example XXV until a substantially homogeneous composition is obtained. The soap composition manifests a characteristic "sandal cologne" aroma having green, oily, pumpkin-like notes.

EXAMPLE XXVII

Preparation of a Soap Composition

A total of 100 g of soap chips produced from unperfumed sodium base toilet soap made from tallow and coconut oil is mixed with 1 g of tricyclene-9-butanone produced according to the process of Example VII until a substantially homogeneous composition is obtained. The soap composition manifests a sandalwood character with green, pumpkin-like oily notes.

EXAMPLE XXVIII

Preparation of a Detergent Composition

A total of 100 g of a detergent powder sold under the trademark "RINSO" are mixed with 0.15 g of a perfume composition containing the mixture obtained in Example XXV until a substantially homogeneous composition having a "sandal cologne" fragrance with green, pumkin-like oily notes is obtained.

EXAMPLE XXIX

Preparation of a Cosmetic Base

A cosmetic powder is prepared by mixing 100 g of talcum powder with 0.25 g of the perfume composition of Example XXV in a ball mill. A second cosmetic powder is similarly prepared except that the mixture produced in Example XXV is replaced with the product produced in Example VII. The cosmetic powder containing the material of Example XXV has a "sandal cologne" fragrance with a green, oily character. The cosmetic powder produced using this material of Example VII has a sandalwood-like aroma with green, pumpkin-like, oily notes.

EXAMPLE XXX

Liquid Detergent Containing Tricyclene-9-butanone

Concentrated liquid detergents with s sandalwood-like odor containing 0.2, 0.5 and 1.2% of the product produced in accordance with the process of Example VII, tricyclene-9-butanone, are prepared by adding the appropriate quantity of tricyclene-9-butanone to the liquid detergent known as P-87. The sandalwood aroma of the liquid detergent increases with increasing concentration of the tricyclene-9-butanone of this invention.

EXAMPLE XXXI

Preparation of Cologne and Handkerchief Perfume

The composition of Example XXV is incorporated in a cologne having a concentration of 2.5% in 85% aqueous ethanol; and into a handkerchief perfume in a concentration of 20% (in 95% ethanol). The use of the composition of Example XXV affords a distinct and definite "sandal cologne" aroma having a warm sandalwood-like character to the handkerchief perfume and to the cologne.

EXAMPLE XXXII

Cologne and Handkerchief Perfume

The tricyclene-9-butanone produced by the process of Example VII is incorporated into a cologne having a concentration of 2.5% in 85% ethanol; and into a handkerchief perfume in a concentration of 10% (in 95% ethanol). The tricyclene-9-butanone produced in Example VII affords a distinct and definite sandalwood aroma with green, pumpkin-like, sandalwood-oily notes to the handkerchief perfume and to the cologne.

What is claimed is:

1. A perfume composition comprising a tricyclic compound having the structure:

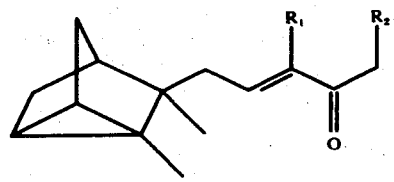

wherein $R_1$ and $R_2$ are each selected from the group consisting of hydrogen or methyl, at least one of $R_1$ or $R_2$ being hydrogen and at least one adjuvant selected from the group consisting of natural perfume oils, synthetic perfume oils, alcohols, aldehydes, other ketones, nitriles, esters, lactones and hydrocarbons.

2. The perfume composition of claim 1 wherein $R_1$ and $R_2$ are each hydrogen.

3. A cologne composition comprising a tricyclic compound having the structure:

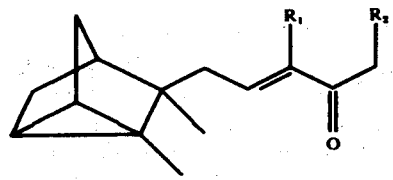

wherein $R_1$ and $R_2$ are each selected from the group consisting of hydrogen or methyl, at least one of $R_1$ or $R_2$ being hydrogen and at least one adjuvant selected from the group consisting of natural perfume oils, synthetic perfume oils, alcohols, aldehydes, other ketones, nitriles, esters, lactones and hydrocarbons. ethanol and water.

4. The cologne composition of claim 3 wherein $R_1$ and $R_2$ are each hydrogen.

* * * * *